United States Patent [19]

Gray

[11] Patent Number: 5,763,586
[45] Date of Patent: Jun. 9, 1998

[54] EXTRACTION OF PROTEINS FROM NATURALLY OCCURING MEMBRANES

[75] Inventor: Don N. Gray, Sylvania, Ohio

[73] Assignee: Anatrace, Inc., Maumee, Ohio

[21] Appl. No.: 747,670

[22] Filed: Nov. 12, 1996

Related U.S. Application Data

[63] Continuation of Ser. No. 279,374, Jul. 22, 1994, Pat. No. 5,674,987.

[51] Int. Cl.$^6$ .................... C07H 15/20; C07H 1/00; C07K 1/14
[52] U.S. Cl. .................... 536/4.1; 536/18.5; 536/1.86; 536/120; 514/25; 530/412; 530/426
[58] Field of Search .................... 536/4.1, 18.5, 536/18.6, 120; 514/25; 30/412, 426

[56] References Cited

U.S. PATENT DOCUMENTS

| | | | |
|---|---|---|---|
| 4,713,447 | 12/1987 | Letton | 536/18.6 |
| 4,950,743 | 8/1990 | McCurry et al. | 536/18.6 |
| 5,037,992 | 8/1991 | Ward et al. | 558/36 |
| 5,266,690 | 11/1993 | McCurry et al. | 536/18.6 |

FOREIGN PATENT DOCUMENTS

| | | |
|---|---|---|
| 132 043 | 1/1985 | European Pat. Off. . |
| 411 980 | 2/1991 | European Pat. Off. . |
| 90 07516 | 12/1990 | WIPO . |

OTHER PUBLICATIONS

"Crystallization of Mitochondrial Ubiquinol–Cytochrome c Reductase", Biochemistry, vol. 30(9):2303–2306, (1991).
"Solubilization and Reconstitution of Membrane Proteins of *Escherichia Coli* Using Alkanoyl–N–Methylglucamides", Biochem. J., 207: 363–366, (1982).
J. Biochem., 95:1349–1353, (1984).
"N–D–gluco–N–Methylalkanamide Compounds, A New Class of Non–Ionic Detergents for Membrane Biochemistry", Biochem. J. 207:363–366, (1982).

*Primary Examiner*—John Kight
*Assistant Examiner*—Howard C. Lee
*Attorney, Agent, or Firm*—Jim Zegeer, Esq.

[57] ABSTRACT

The extraction of proteins from selected naturally occurring membranes without any harmful, adverse, or other deleterious effect(s). In one preferred embodiment the detergent is prepared from the reaction of a cycloalkyl aliphatic alcohol and a saccharide.

13 Claims, 2 Drawing Sheets

EXTRACTION OF PROTEINS FROM NATURALLY OCCURING MEMBRANES

This is a continuation of application Ser. No. 08/279,374, filed Jul. 22, 1994, now U.S. Pat. No. 5,674,987.

BACKGROUND AND BRIEF DESCRIPTION OF THE INVENTION

This invention relates to the extraction of proteins from naturally occurring membranes.

In the prior art proteins have been extracted with detergents from natural occurring membranes. Often, these proteins have been compromised during extraction so as to lose the natural function and/or benefits of the protein. In accordance with this invention, the extraction of many proteins from natural membranes is accomplished without any harmful, adverse, or other deleterious effect(s).

In accordance with the practice of this invention, there is provided a process for extracting one or more proteins from a natural membrane with a detergent prepared from the reaction of a cycloalkyl aliphatic alcohol and a saccharide.

More particularly, in accordance with this invention, there is provided a detergent for the extraction of one or more proteins from a naturally occurring membrane to an aqueous solution, each protein being extracted free of harmful, adverse or deleterious effect(s) by the use of a detergent prepared from the reaction of a cycloalkyl aliphatic alcohol and a saccharide.

As used herein cyclo alkyl aliphatic alcohol is defined as compounds represented by the structure:

wherein R is cyclopropyl, cyclobutyl, cyclopentyl, cyclohexyl, cycloheptyl, and cyclooctyl and n is 1 to 10, typically 1 to 6.

In one preferred embodiment, R is cyclo hexyl and n is 6. ak include 6-cyclohexyl, 5-cyclohexylpentanol, 4-cyclohexylbutanol and the like.

As used herein saccharide is defined as mono, di, and/or tri saccharide. Examples include glucose, maltose, maltotriose and sucrose.

The practice of this invention provides proteins which have not been compromised during the extraction process and which are crystallizable. Such crystallized proteins may be subject to X-ray analysis for determination of their three-dimensional structure.

The understanding of protein function is greatly enhanced by the availability of three-dimensional structural information obtained by X-ray crystallography. Heretofore, the large, well-ordered three-dimensional crystals required for X-ray analyses have been difficult to produce for membrane proteins since they tend more naturally to form two-dimensional arrays. A further complicating factor in dealing with membrane proteins is the requirement for detergents to solubilize and stabilized the native structure. In the crystallization of membrane proteins, the structure and purity of the detergent are critical factors. Detergents which possess a more rigid hydrophobic tail by inclusion of saturated cyclic rings have been synthesized. These types of detergents are of extreme interest in the biological study and crystallization of membrane proteins due to unique characteristics. In the practice of this invention, there is provided detergents with the hydrophobic tail consisting of cyclohexyl derivatives and the hydrophilic head consisting of maltoside or glucoside.

This invention relates to the preparation and use of detergents which include a hydrophobic tail containing one or more cyclic ring structures and a hydrophilic head. The hydrophobic tail is more rigid by the incorporation of one or more cyclic ring structures such as cyclohexyl, cyclopentyl, cyclopropyl etc. The hydrophilic head is often glucopyranoside or maltopyranoside, but is not limited to these functional groups. Other acceptable functional head groups consist of but are not limited to amine oxide, sulfate, fructofuranosyl-glucopyranoside, and ammonium bromide. A particularly useful series consists of a cyclohexyl-$(CH_2)_n$-malto-sides.

The detergents described herein are particularly useful in the extraction of membrane proteins. They are non denaturing and some detergents have been shown to extract membrane proteins selectively thus saving time and effort in the purification of the extracted membrane protein. In addition they can be used to crystallize membrane proteins where their cyclic ring structure has been shown to have unique properties.

Advances in the understanding of the structure and function of proteins have relied heavily on the use of X-ray crystallographic analysis of single protein crystals (A. McPherson "Preparation and Analysis of Protein Crystals", Wiley, N.Y. (1982)). Indeed it was this type of analysis that ushered in the modern era of the science of molecular biology (J. D. Watson and F. H. Crick, *Nature*, 171, 737–738 (1953)) and the business of biotechnology (P. Daly, *The Biotechnology Business*, Pinter London (1985). The spatial analysis of proteins was accomplished using carefully grown, well ordered crystals of sufficient size. Membrane proteins, because of their limited solubility, present special problems in growing adequate crystals (W. Kuehlbrandt, *Quart. Rev. Biophys.*, 21, 429–477 (1988)). There has been a great need expressed for new, pure, structurally defined detergents for purifying and analyzing membrane proteins (P. Rosevear, T. VanAken, J. Baxter and S. Ferguson-Miller, *Biochem.*, 19 4108 (1980); H. W. Chang, and F. Bock, *Anal. Biochem.*, 104, 112 (1980); D. B. Datta, *Membrane Biochemistry*, Floral Pub., Madison, Wis., Chapter 5, PP 789–203 (1987).

While there has been much progress made in understanding the structure of membrane proteins during the last decade the present knowledge is not as great as for soluble proteins. Yet membrane proteins are of critical importance in determining the functional properties of cells, carrying out selective transport of ions and metabolites, acting as receptors for hormones and growth factors and involved in a variety of energy generating and drug detoxifying systems.

Biological membranes consist of a lipid bilayer of approximately 50 angstroms in thickness. Membrane lipids are amphiphiles with hydrophilic heads and hydrophobic tails that self-associate into a bilayer structure with a hydrophobic interior and hydrophilic surface.

Proteins that are intrinsic to membranes have areas that associate with the hydrophobic core of the bilayer, as well as portions that experience the aqueous environment at the membrane surface. In order to purify such molecules and retain their native structure, it is necessary to remove the lipid and replace it with a substitute molecule that will cover the hydrophobic surfaces and exclude water, but will not form an extended bilayer. Detergents can perform this function.

Detergents are small amphophilic molecules that mimic lipids in having both hydrophobic and hydrophilic portions, but tend to form small micelles rather than large bilayers. Most detergents used for membrane protein crystallization have a single hydrocarbon tail of 8–12 carbon atoms (W. Kuehlbrandt, *Quart. Rev. Biophys.*, 21, 429–477 (1988)) but a variety of hydrophilic heads. Detergent types that have found utility fall into broad categories according to head group chemistries including ionic zwitterionic and non-ionic types. All detergents, regardless of type, function to solubilize proteins because of their ability to form micelles, which break up the membrane bilayer and provide a substitute environment for the proteins. The micelle size of utility for solubilizing membrane proteins falls into the narrow range of 40–60 angstroms in diameter, while the most useful non-ionic detergents have even a narrower range of 40–50 angstroms (W. Kuehlbrandt, *Quart. Rev. Biophys.*, 21, 429–477 (1988)), presumably because of the need to provide a hydrophobic phase of similar dimensions to the membrane.

In addition to size, it is also important to know at what concentration the detergent molecules self-associate to form thermodynamically stable aggregates called micelles. The formation of micelles by amphophilic molecules above a narrow concentration range called the Critical Micelle Concentration (CMC) has vital implications for the action of detergents in biological systems. In fact a CMC that is "too high" or "too low" may render the detergent not useful. A CMC above 40 mM for practical, technical and economical reasons, would make a detergent inappropriate as a solubilizing and crystallizing agent for membrane proteins. Detergents with moderately high CMCs (20–40 mM), may still be useful if they gently and effectively solubilize membrane proteins at a reasonable cost per gram. Detergents with CMCs of 1–20 mM readily form micelles at low concentrations, yet have high enough CMCs to allow their facile removal or exchange. Amphophilic molecules with low CMCs (less than 1 mM), pose limitations to their usefulness due to difficulties in controlling detergent concentration and in ensuring their removal or exchange.

In order to crystallize membrane proteins, it is necessary that they be obtained in a pure, monodisperse state such that each protein molecule is surrounded by a detergent coating, often equivalent to a single detergent micelle, that keeps the protein in solution and in an active state (M. Zulauf, "Detergent Phenomena in Membrane Proteins", in *Crystallization of Membrane Proteins*, H. Michel ed., CRC Press, Boston, Mass., 53–72 (1991)). If detergent is removed, the proteins will self-associate and precipitate. However, if the detergent coat is too bulky it may prevent the proteins from interacting via their hydrophilic surfaces to form crystals.

Type II crystals as defined by Michel (H. Michel, *J. Molec. Biol.*, 158, 567–572 (1982)) have the apolar ends of detergents bound to the hydrophobic patches on the membrane proteins, where lipids once bound. The polar ends of the detergents form the interprotein contacts. The hydrophilic areas of the protein mediate crystal formation. Therefore, the structure of the detergent and its micelle size may be crucial in determining whether crystallization can occur.

N-octyl-β-D-glucopyranoside (OG) is a mild, nonionic detergent that forms relatively small micelles which appear to be effective for solubilizing some proteins and permitting crystal formation (R. M. Garavito & J. P. Rosenbusch, *Meth. Enzymol.*, 125, 309.328 (1986)). If the protein is large and has an extensive hydrophilic domain, such as the bacterial reaction center (H. Michel, *J. Molec. Biol.*, 158, 567–572 (1982)), the detergent and micelle size may not be the limiting factor. Hence, the reaction center was crystallized using N,N-dimethyl-dodecylamine oxide (LDAO), which has a relatively large size and micelle aggregation number compared to octylglucose. Nevertheless, for the general purpose of membrane protein crystallization a smaller size may be critical.

The process of obtaining single crystals of proteins is fraught with difficulties under any circumstances. Methods such as direct precipitation, concentration via dialysis, vapor diffusion, temperature variation, have all been used (G. L. Gilliland and D. R. Davis, *Meth. Enzymol.*, 104, 370–381 (1984)). Garavito and Rosenbuch have given a detailed procedure for producing crystals from the membrane protein bacterial porin (R. M. Garavito and J. P. Rosenbusch, *Meth. Enzymol.*, 125, 309–328 (1986)). Kuehlbrandt has written a thorough, recent review on the crystallization of membrane proteins (W. Kuehlbrandt, *Quart. Rev. Biophys.*, 21, 429–477 (1988)). No matter what method is used the membrane protein must be solubilized and purified first, introducing the further complicating variable of a detergent.

DETAILED DESCRIPTION OF THE INVENTION

Figure 1:
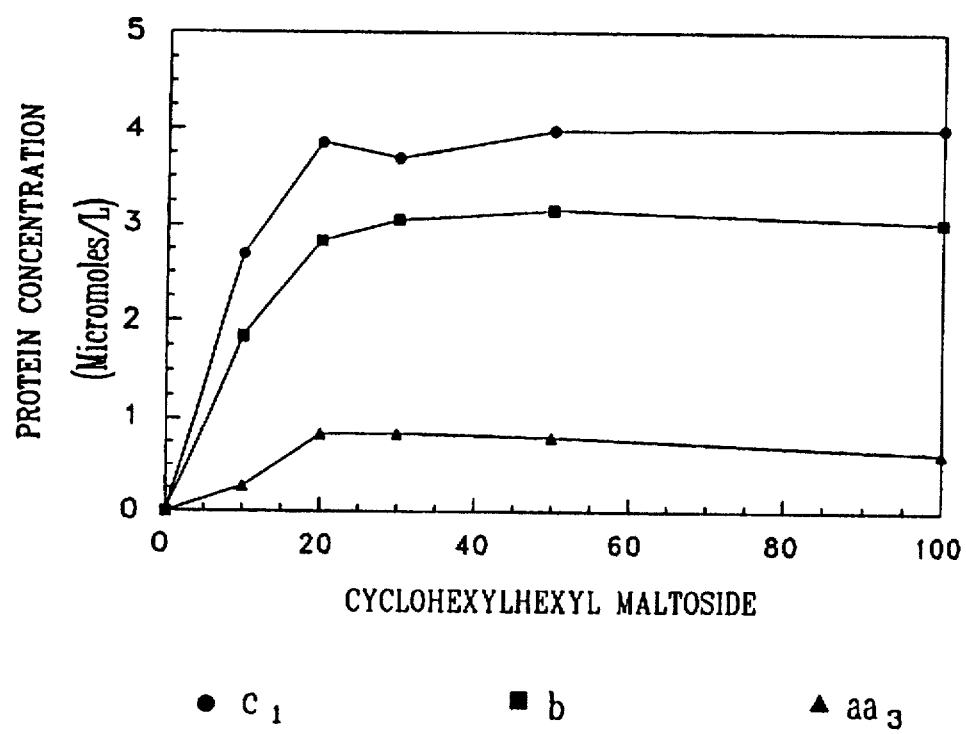
FIG. 1 is a graph showing the effectiveness of cyclohexylhexyl maltoside as a solubilizing agent for mitochondrial membranes.

These detergents are synthesized by first preparing an acetobromomaltose derivative as described in the literature (P. Rosevear, T. VanAken, J. Baxter and S. Ferguson-Miller, *Biochem.*, 19, 4108 (1980) and T. VanAken, S. Foxall-VanAken, S. Castelman and S. Ferguson-Miller, *Meth. Enzym.*, 125, 27–32 (1986)). Acetobromomaltose is reacted with an alcohol, such as cyclohexylmethanol, cyclohexyethanol, up to and including cyclohexylhexanol, in the presence of silver carbonate as the catalyst. These alcohols are commercially available except for cyclohexylpentanol and cyclohexylhexanol. A typical Grignard reaction using cyclohexylpropanol and cyclohexylbutanol reacted with ethylene oxide is used to prepare cyclohexylpentanol and cyclohexyhexanol, respectively.

After filtering and concentrating the reaction mixture by rotary evaporation, it is reacted with 0.01N $H_2SO_4$ to hydrolyze any ortho ester formed as a side product during the condensation reaction. The solution is neutralized by adding pyridine and concentrated to a syrup. A deacetylation is carried out by dissolving the syrup in methanol/triethylamine/water (2:1:1) and letting it stand overnight. The detergent is purified by chromatography on a Dowex 1 ion exchange resin.

The aliphatic bridging group is essential to obtain the unique properties of these detergents since cyclohexyl maltoside has been synthesized and has too high a critical micelle concentration to be useful either for extraction or crystallization of membrane proteins (N. Mitsuo, H. Takeichi, and T. Satoh, *Chem. Pharm. Bull.*, 32, 1183–1187, (1984)). In this particular series of detergents the chain lengths from cyclohexyl butyl to cyclohexyl hexyl have been found to be the most effective in extraction and crystallization of membrane proteins. Other series with cyclopropyl, cyclobutyl, etc ring structures would possess different effectiveness for each member of the series.

EXAMPLE ONE

Synthesis of Cyclohexylmethyl Maltoside

Part A

A 50% weight/volume solution of acetobromomaltose in dichloromethane is added to a 5 liter 3 neck round bottom flask. The entire bottom of this flask is covered with aluminum foil. An additional 2 liters of dichloromethane along with 500 g of cyclohexylmethanol, 8 g of iodine, 100 g silver carbonate and 300 g drierite is also added. This solution is allowed to react for 20 hours, with constant stirring, at room temperature while in the dark. This mixture is filtered through a glass scintered funnel using Celite 503 (Fisher Scientific brand of diatomaceous earth) as a filtering aid. The collected filtrate is concentrated to a thick consistency using a water aspirator.

Part B

Ten mL of concentrated sulfuric acid is added to 200 mL of deionized water (D.I. $H_2O$) and then further diluted with acetone to a final volume of 2 L. This acidic solution is added to the concentrated filtrate prepared in Part A and thoroughly mixed for 30 minutes at room temperature, followed by the addition of 80 mL pyridine. This solution is concentrated via a water aspirator to a thick consistency.

Part C

A solution consisting of 0.5 L D.I. $H_2O$, 0.5 L triethylamine and 1.0 L methanol is added to the concentrate obtained in Part B and allowed to react for 20 hours at room temperature with constant stirring. This solution is concentrated via a water aspirator to a final volume of about 2.0 L. When poured into a 2 L. separatory funnel, the liquid separated into two layers. The bottom aqueous layer was drained and saved. The top layer was washed three times with 500 mL of hot D.I. $H_2O$, each time the aqueous layer is drained and saved. When combined, the entire volume of the aqueous phases is about 2 L. It was concentrated to about 500 mL by rotary evaporation.

Part D

Thin layer chromatography (TLC) is done on both the top and bottom layers to determine the location of the detergent, cyclohexylmethyl maltoside. TLC was done as described by Rosevear et al., in Biochemistry, 19, 4108–4115 (1980). When the location of the detergent is identified, the solution is applied to a Dowex ion exchange resin column as described in part E. For cyclohexylmethyl- and cyclohexylpentyl maltosides the aqueous phase contained the detergent, while cyclohexylethyl, -propyl, -butyl, and -hexyl maltosides were found in the non-aqueous or organic phase.

Part E

Approximately 1 kg of Dowex resin, Dowex-1-chloride strongly basic, 200–400 dry mesh, Catalog number 21,743-3, lot# 06510 EV, was converted to the hydroxide form by allowing the resin to react with 2N NaOH for one hour, then by filtering and washing with an additional 15 L of 2N NaOH. The converted resin was washed further with 15 L of D.I. $H_2O$ followed by 3 L of methanol. A glass column measuring 10 cm×90 cm was filled with this resin. After equilibrating the column in spectral grade methanol, 500 mL of concentrated combined aqueous phases is applied to the resin column. The flow rate is set at 26 mL/min. The eluant is collected in fractions of about 260 mL, and TLC is done as described in Part D to determine the location of the detergent.

Part F

The methanol in each fraction is removed by rotary evaporation with a rotating shaft evaporator connected to a water aspirator. The residue (detergent) is analyzed by high performance liquid chromatography (HPLC) to determine alpha and beta anomer content. A silica HPLC column (Econosil SI 10U, Catalog number 60090 Alltech Associates, Inc.) measuring 250×4.6 mm is used to ascertain alpha and beta isomers of the detergent. The mobile phase is 92% butyl acetate/8% methanol and the flow rate set at 0.8 mL/min. The detergents are detected by refractive index and the peaks integrated to determine the percent composition with respect to alpha and beta isomers.

Each fraction is also analyzed by HPLC for the presence of starting alcohol (cyclohexylmethanol). A $C_{18}$ HPLC column (All-tech Associates, Inc., catalog number 60096) measuring 250×4.6 mm is used for this analysis. The mobile phase is 75% acetonitrile/25% D.I. $H_2O$ with a flow rate of 1.2 mL/min. The alcohols are detected by refractive index. The amount of alcohol present is determined by comparing the results to a standard curve prepared by injecting various concentrations of the starting alcohol.

Fractions containing less than 2% alpha anomers of cyclohexylmethyl maltoside and less than 0.005% starting alcohol are pooled and lyophilized. Fractions containing detergents with more than 2% alpha isomers and more than 0.005% alcohol are pooled and then purified by rechromatograping on the Dowex resin column.

EXAMPLE 2

Synthesis of Cyclohexylhexyl Maltoside

Part A

A 50% weight/volume solution of acetobromomaltose in dichloromethane is added to a 5 liter 3 neck round bottom flask that is covered with aluminum foil. Two liters of dichloromethane along with 500 g of cyclohexylhexanol, 8 g of iodine, 100 g silver carbonate and 300 g drierite is also added. After reacting for 20 hours in the dark at room temperature and constant stirring the mixture is filtered through a glass scintered funnel using Celite 503 as a filtering aid. The collected filtrate is concentrated to a syrup by rotary evaporation.

Part B

Ten mL of concentrated sulfuric acid is added to 200 mL of D.I. $H_2O$ and further diluted with acetone to a final volume of 2 L. This acidic solution is added to the concentrated filtrate prepared in Part A and thoroughly mixed for 30 minutes at room temperature, followed by the addition of 80 mL pyridine. Again, this solution is concentrated to a syrup via rotary evaporation.

Part C

The concentrate of Part B is added to a solution of 0.5 L D.I. $H_2O$, 0.5 L triethylamine and 1.0 L methanol and allowed to react for 20 hours at room temperature with constant stirring. This solution is concentrated to a final volume of about 2 L by rotary evaporation. When poured into a 2 L separatory funnel, the liquid separated into two layers. The bottom aqueous layer was drained and saved. The top layer was washed three times with 500 mL hot D.I. $H_2O$, each time the aqueous layer is drained and combined with the other aqueous phases. The combined solutions, about 2 L is concentrated to a final volume of 500 mL by rotary evaporation.

Part D

Analysis of both the top and bottom layers by TLC (as described in Part D of example number 1) is done to determine the location of cyclohexylhexyl maltoside. The detergent is found in the non-aqueous phase and is applied to a Dowex ion exchange resin column as described in part E of example number 1. The glass column which measures 90×10 cm is equilibrated with methanol and the flow rate set at 26 mL/min. The eluent is collected in fractions of about 260 mL, and TLC is done to determine the location of the detergent. Unreacted alcohol elutes well before the cyclohexylhexyl maltoside and the alpha isomer of the detergent is found in the early fractions. The presence of both unreacted alcohol and alpha anomers is determined a HPLC method described in Part F of example number 1.

Fractions containing less than 2% alpha anomers of cyclohexylhexyl maltoside and less than 0.005% starting alcohol were pooled and lyophilized. Fractions containing more than this are pooled and purified again by rechromatographing on the Dowex ion exchange column.

DISCUSSION OF FIGS. 1 AND 2 SOLUBILIZING PROTEIN WITH NEW DETERGENTS

Figure 2:
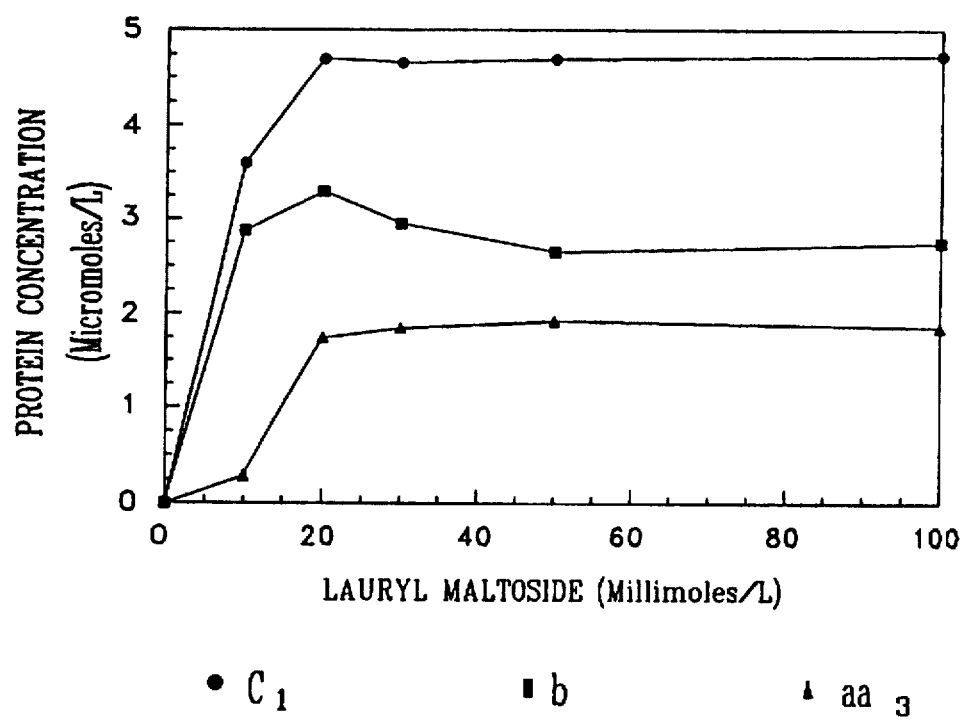
FIG. 2 is a graph showing the effectiveness of detergents of this invention.

The effectiveness of cyclohexylhexyl maltoside as a solubilizing agent for mitochondrial membranes is shown in FIG. 1. The optimal cyclohexylhexyl maltoside concentration for complete solubilization of rat liver mitochondria is 20 mM, at 20 mg protein/mL. The effectiveness of this new detergent is comparable to lauryl maltoside, which also requires 20 mM concentrations, in solubilizing rat liver mitochondrial cytochromes, see FIG. 2. The general procedure for the extraction of mitochondrial membranes, as described in Rosevear et al., Biochemistry 19, 4108–4115 (1980) is given.

Rat inner mitochondrial membranes are solubilized at varying concentrations of detergent in 0.66M sucrose, 0.5M KCl and 0.05M Tris-HCl, pH 8. The presence of cytochromes in the 45000 g×1 hour supernatant is determined by measuring the dithionite-reduced minus the ferricyanide-oxidized difference spectra from 500 to 650 nm with a Cary 17 dual-beam scanning spectrophotometer. The concentrations are calculated from the millimolar extinction coefficients for cytochrome $aa_3$ at 605 minus 630 nm of 24, cytochrome b at 560 minus 575 nm of 23.4, and cytochrome $c_1$ at 553 minus 542 nm of 18.7. No corrections were made for the contributions of the other cyctochromes at the specific wavelengths.

Having described the invention what is claimed is:

1. A diagnostic detergent for the extraction and purification of membrane proteins, said detergent having a structure comprised of a moiety possessing at least one cyclic aliphatic moieties resulting in a hydrophobic tail connected to a hydrophilic head, said hydrophilic head being selected from a saccharide of the group comprising aldose and ketose, and wherein the attachment of said hydrophobic tail to said hydrophilic head is covalent and the attachment of the saccharide moiety is by way of the acetal-hydroxy group to form an ether linkage.

2. A diagnostic detergent for the extraction and purification of membrane proteins, said detergent comprising a selected one of a pendant or terminal cyclohexyl group, covalently attached to a methylene chain of one to ten members, which is connected covalently to an hydrophilic head which may be either charged or highly polar.

3. The diagnostic detergent of claim 2 wherein the hydrophilic head group is a maltoside group.

4. A process for the synthesis of the diagnostic detergents of claim 3 in which acetobromomaltose is reacted with the appropriate alcohol:

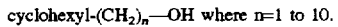

cyclohexyl-$(CH_2)_n$—OH where n=1 to 10.

5. The diagnostic detergent in claim 2 wherein said hydrophilic head group is the glucoside group.

6. The process for preparing the diagnostic detergent as in claim 1 consisting of the reaction of a selected active mono or disaccharide derivative with an alcohol selected from a class of alcohols consisting of an aliphatic cyclic ring structure with the methylene groups separating the cyclic aliphatic moiety from the carbinol group.

7. The process for preparing a diagnostic detergent as in claim 2 consisting of the reaction of a selected acid mono or disaccharide derivatives with an alcohol selected from a class of alcohols wherein a cyclohexyl or substituted cyclohexyl ring structure with methylene groups separating the cyclic aliphatic moiety from the carbinol group.

8. A process for producing a diagnostic detergent for the extraction and purification of membrane proteins which comprises reacting a cyclo aliphatic alcohol and a saccharide selected from the group consisting of aldose and ketose to synthesize a detergent which will extract proteins from a membrane to an aqueous solution.

9. A process for producing a diagnostic detergent which comprises reacting a cyclo alkyl aliphatic alcohol and a saccharide so as to synthesize a detergent which will extract one or more proteins from a natural membrane to an aqueous solution.

10. A process for extracting one or more proteins from a naturally occurring membrane comprising subjecting said membrane to the diagnostic detergent of claim 1.

11. The compound 5-cyclohexylpentyl maltoside.

12. The compound 5-cyclohexylpentyl glucoside.

13. The compound 6-cyclohexylhexyl glucoside.

* * * * *